United States Patent [19]

Dybas et al.

[11] 4,094,976
[45] June 13, 1978

[54] ANTICOCCIDIAL CYCLICAMINO ETHANOLS AND ESTERS THEREOF

[75] Inventors: Richard A. Dybas, Somerville; Donald W. Graham, Mountainside; Jeannette E. Brown, Summit, all of N.J.

[73] Assignee: Merck & Co., Inc., Rahway, N.J.

[21] Appl. No.: 755,366

[22] Filed: Dec. 29, 1976

Related U.S. Application Data

[63] Continuation of Ser. No. 586,006, Jun. 11, 1975, abandoned.

[51] Int. Cl.² .................. A61K 31/63; A61K 31/65; A61K 31/40
[52] U.S. Cl. .................................... 424/228; 424/229; 424/244; 424/251; 424/264; 424/267; 424/274
[58] Field of Search ............... 424/228, 229, 244, 251, 424/264, 267, 274

[56] References Cited

PUBLICATIONS

Balint et a., —Chem. Abst. vol. 79 (1973) p. 18316y.
Martinez Roldan et al. —Chem. Abst. vol. 80 (1974) p. 82642z.
Atare et al.—Chem. Abst. vol. 67 (1967) pp. 107, 268d.
Morrow et al. —Chem. Abst. vol. 79 (1973) pp. 100, 795n.

*Primary Examiner*—Sam Rosen
*Attorney, Agent, or Firm*—Walter Patton; Harry E. Westlake, Jr.

[57] ABSTRACT

Novel anticoccidial poultry compositions comprising an anticoccidially effective amount of a compound of the formula:

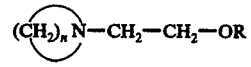

wherein $n$ is 3, 4 or 5 and R is hydrogen or an acyl radical derived from a non-toxic carboxylic acid or a non-toxic acid addition salt thereof methods of combatting poultry coccidiosis, novel compounds and methods of preparing these novel compounds.

15 Claims, No Drawings

4,094,976

ANTICOCCIDIAL CYCLICAMINO ETHANOLS AND ESTERS THEREOF

This is a continuation of application Ser. No. 586,006 filed June 11, 1975, now abandoned.

BACKGROUND OF THE INVENTION

Coccidiosis is a common and widespread poultry disease caused by species of protozoan parasites of the genus Eimeria. The most important of these species are *E. maxima, E. acervulina, E. tenella, E. necatrix* and *E. brunetti.* In turkeys, *E. meleagridis* and *E. adenoides* are also causative organisms of coccidiosis. When left untreated, the disease leads to poor weight gain, reduced feed efficiency and high mortality. For these reasons, the control of coccidiosis is highly important to the poultry industry. Although *E. tenella* and *E. necatrix* cause the most lethal forms of the disease, it is known that infections due to other species, and particularly to the so-called intestinal species such as *E. acervulina, E. brunetti* and *E. maxima,* also present a serious economic problem.

DETAILS OF THE INVENTION

It has been found that compounds of the formula:

$$(CH_2)_n \quad N-CH_2-CH_2-OR \quad (I)$$

wherein $n$ is 3, 4 or 5 and especially 4, and R is hydrogen or an acyl radical derived from a non-toxic carboxylic acid or a non-toxic acid addition salt thereof, exhibit significant activity against the poultry disease coccidiosis, and especially against *E. tenella.* These compounds also have the additional desirable property of potentiating certain sulfa drugs, or sulfa drugs in combination with 2,4-diamino-5-phenyl (or benzyl)-6-$C_{1-5}$alkyl (or hydrogen)-pyrimidine compounds in coccidiosis control.

The radical R may be derived from a non-toxic carboxylic acid, such as a $C_{1-10}$alkanoyl, such as formyl, butyryl, isobutyryl and especially acetyl, hexanoyl or actanoyl; a substituted $C_{1-5}$alkanoyl where the substituent is halophenyl (p-chlorophenyl) or diphenyl or a carbocyclic $C_{1-5}$alkanoyl, 1-adamantylacetyl; 1-adamantylcarbonyl; a benzoyl such as benzoyl and especially p-nitrobenzoyl; a heterocyclic carbonyl such as nicotinyl and expecially orotoyl; a $C_{1-10}$alkane dicarbonyl such as adipyl and especially monosuccinyl; or especially hydrogen.

The non-toxic acid addition salts may be derived from the following acids: acetic, citric, hydroiodic, hydrobromic, lactic, nitric, phosphoric, sulfuric, tartaric, valeric, phthalic, and especially hydrochloric.

The sulfa drugs may be sulfabenz, sulfachloropyrazine, sulfachloropyridazine, sulfadiazine, sulfadimethoxine, sulfaguanidine, sulfamerazine, sulfamethazine, sulfanitran and especially sulfaquinoxaline or a compound of the formula:

$$R_3O-\underset{N\diagdown_S\diagup N}{\parallel\phantom{xx}\parallel}-\underset{R_1}{\overset{|}{N}}-SO_2-\bigotimes-\overset{H}{\underset{|}{N}}-R_2$$

wherein
R is $C_{2-5}$alkenyl, such as crotyl, methallyl and especially allyl, $C_{2-5}$alkynyl, such as 2-butynyl, 3-butynyl, 2-propynyl or $C_{2-5}$alkyl such as ethyl, n-propyl, isopropyl, butyl;
$R_1$ is an alkali metal or especially hydrogen; and $R_2$ is acyl, such as benzoyl or $C_{1-5}$alkanoyl such as acetyl, propionyl or butyryl or especially hydrogen.

Representative of the 2,4-diamino-5-phenyl (or benzyl)-6-$C_{1-5}$alkyl (or hydrogen)-pyrimidines are:

2,4-diamino-5-(p-chlorophenyl)-6-methylpyrimidine,
2,4-diamino-5-(p-chlorophenyl)-6-n-propylpyrimidine,
2,4-diamino-5-(p-chlorophenyl)-6-n-amylpyrimidine,
2,4-diamino-5-(3',4'-dimethoxybenzyl)-6-hexylpyrimidine,
2,4-diamino-5-(3',4'-dimethoxybenzyl)-pyrimidine,
2,4-diamino-5-(3',4'-dimethoxy-6'-methylbenzyl)-pyrimidine,
and especially 2,4-diamino-5-(p-chlorophenyl)-6-ethyl-pyrimidine(pyrimethamine).

The novel anticoccidial compositions are intimately dispersed in or admixed with an inert edible carrier or diluent. Such carrier is ordinarily an element of animal sustenance, i.e. one that is or may be an ingredient of the animal feed, and that has some degree of nutritive value for the animal. These solid compositions are the so-called feed supplements or feed premixes which contain large amounts, and which are designed for the poultry feed either directly or after an intermediate dilution or blending step. Examples of nutritive carriers or diluents suitable for such compositions are animal feed ingredients such as distillers'dried grains, corn meal, citrus meal, fermentation residues, ground oyster shells, wheat shorts, molasses solubles, corn cob meal, edible vegetable substances, toasted dehulled soya flour, soybean mill feed, antibiotic mycelia, soya grits, grits, crushed limestone, and the like. The coccidiostat in intimately dispersed or admixed throughout such solid carrier by techniques such as grinding, stirring, milling, or tumbling. By selecting proper diluents and by altering the ratio of carrier to active ingredient, compositions of any desired concentration may be prepared. Formulations containing from about 10 to 30% by weight of the anticoccidial agent are particularly suitable for addition to poultry feedstuffs. The active compound is usually dispersed or mixed uniformly in the diluent, but in some instances may be sorbed on the carrier. Since it is convenient for the feed manufacturer to use about one pound of feed supplement for each ton of finished feed, the preferred concentration in the supplement is frequently a function of the level of active ingredient desired in the finished feed.

The cyclicamino ethanols or esters thereof and especially 2-pyrrolidinoethanol may be incorporated in anticoccidially effective amounts into feed compositions or in drinking water, alone, in combination with a sulfa drug and especially sulfaquinoxaline or in combination with a sulfa drug and especially sulfaquinoxaline and a pyrimidine and especially pyrimethamine. The anticoccidial composition may contain as active ingredients from about 0.2 to 0.025% and especially 0.1 to 0.05% of a cyclicaminoethanol or ester thereof; 0.2 to 0.0125% and especially 0.05 to 0.025% of a cyclicaminoethanol or ester thereof and 0.1 to 0.002% and especially 0.05 to 0.005% of a sulfa drug; or 0.2 to 0.0125% and especially 0.05 to 0.025% of a cyclicaminoethanol or ester thereof, 0.1 to 0.005% and especially 0.05 to 0.005% of a sulfa drug and 0.001 to 0.0001% and especially 0.0005 to 0.0003% of a pyrimidine all expressed in percent by weight of the total feed ration. The optimum dose level will vary somewhat depending on the specific compound employed and the severity of coccidial infection involved. The solid finished feed containing a coccidiostat of this invention dispersed or distributed therein may be any of those usually employed in the poultry raising industry, and are nutritionally adequate ones, normally containing a source of fat, protein, carbohydrate, minerals, and other nutritional factors. The feed containing the desired dose level of coccidiostat is fed ad libitum to the poultry. As will be understood by those skilled in this art, the dose level of drug administered is customarily expressed in terms of concentration in the feed of birds, rather than in terms of poultry weight. The figures, expressed as a percent by weight of feed consumed, may be converted to weight of compound per bird per day by using the table below. For example, if a two week old broiler chick consumes 150 g of feed per kilogram of body weight, and a compound is present in the feed at the 0.2% level, the chick receives 0.3 g of compound per kilogram body weight per day.

Examples of such poultry feed supplements are:

|   |   | lbs. |
|---|---|---|
| A: | 2-Pyrrolidinoethanol | 5.0 |
|   | Wheat middlings | 95.0 |
| B: | 2-Pyrrolidinoethanol | 15.0 |
|   | Wheat shorts | 35.0 |
|   | Distillers' dried grains | 50.0 |
| C: | 2-Pyrrolidinoethanol | 30.0 |
|   | Corn germ meal | 20.0 |
|   | Corn distillers' grain | 50.0 |

These supplements are prepared by mechanical milling or mixing of the ingredients to insure uniform distribution of the active compound.

The feed supplements of the type illustrated are usually further diluted with feed ingredients such as corn meal or soybean meal before being incorporated in the animal feed. In this intermediate processing step the level of coccidiostat is reduced, thus facilitating uniform distribution of the substances in the finished feed which is a nutritionally adequate one, normally containing a source of fat, protein, carbohydrate, minerals, vitamins and other nutritional factors.

It will further be understood by those skilled in this art that special feed supplement formulations and finished animal feed containing vitamins, antibiotics, growth-promoting agents, and other nutritional substances may include the novel anticoccidial compounds of this invention. A typical formulation premix of this type is the following:

| Ingredient | Amount/lb of supplement, grams |
|---|---|
| Riboflavin | 0.64 |
| DL-Calcium pantothenate | 2.10 |
| Niacin | 3.67 |
| Choline chloride | 50.00 |
| Vitamin B$_{12}$ concentrate[1] | 1.30 |
| Procain penicillin | 0.84 |
| Vitamin A (100,000 u./g.) | 3.38 |
| Vitamin D$_3$ (200,000 u./g.) | 0.68 |
| Arsanilic acid | 18.36 |
| Butylated hydroxytoluene | 23.15 |
| DL-Methionine | 23.15 |
| 2-Pyrrolidinoethanol | 23.00 |
| Distillers' grains, to 1 pound | |

[1]milligram

The compounds of this invention may also be administered to poultry by way of the drinking water. When this route is used in the prevention of coccidiosis the treatment levels in the water ore generally about one-half of those that would be used in solid feedstuff, since the birds drink about twice as much as they eat. This method of treatment is advantageously employed in the therapeutic use of these compounds, since poultry infected with coccidiosis consume less solid feed than normal birds. The compounds may be added directly to the drinking water. Alternatively, water-soluble powders may be prepared, in which the coccidiostat is intimately admixed with a suitable carrier, such as dextrose or sucrose, and these powders added to the drinking water of poultry as necessary. Such water-soluble powders may contain any desired concentration of the coccidiostat. Preparations containing from about 0.1 to 20% by weight of active compound are suitable. Liquid formulations intended for addition to the drinking water may contain minor amounts of surfactants, solubilizers, or suspending agents such as dimethylpolysiloxane, polyoxyethylene sorbitan monoleate and propylene glycol.

Some of the cyclicaminoethanols and esters thereof of are novel compounds and make up another aspect of this invention. The compounds may be described as follows:

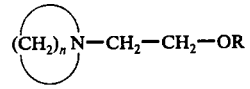

wherein $n$ is 3; and R is hydrogen or an acyl radical derived from a non-toxic carboxylic acid; or $n$ is 4 or 5 and especially 4; and R is formyl, butyryl, isobutyryl or nicotinoyl and especially hexanoyl, octanoyl, 1-adamantylacetyl, 1-adamantylcarbonyl, p-chlorophenylacetyl, orotoyl or monosuccinyl or non-toxic acid addition salts there.

2-(1-Azetidino)-ethanol ($n$ is 3) may be prepared by reacting approximately equal molar amounts of azetidine and a 2-haloethanol, especially 2-bromo or 2-chloroethanol. A mild base, such as an alkali metal carbonate, an alkali metal bicarbonate, an alkaline earth carbonate, an alkaline earth bicarbonate or a tertiary amine and especially a triC$_{1-5}$alkylamine such as diisopropylethylamine or pyridine, may be present in an equimolar amount to the 2(halo)-ethanol to remove the free acid of the reaction. The reaction may be carried out in an inert organic solvent such as chloroform or benzene or excess triC$_{1-5}$alkylamine or pyridine. The reaction is carried out at a temperature or from about 50° C to 130° C. The time of reaction is not critical and the reaction is preferably carried out until it is essentially complete. The pressure is not critical and the reaction is generally carried out at atmospheric pressure in an open system. An inert atmosphere of helium, neon, argon and especially nitrogen may be used. The reaction product may be recovered in the conventional manner, such as by extraction, filtration and evaporation of the solvent.

The esters of the formula:

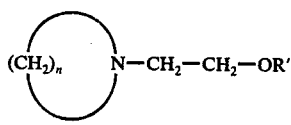

may be prepared in the conventional manner, such as by reacting a cyclicaminoethanol of the formula:

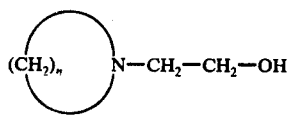

with a compound of the formula:

R'—X wherein n is 3,4 or 5 and especially 4, R' is butyryl, isobutyryl, hexanoyl, octanoyl, 1-adamantylacetyl, 1-adamantylcarbonyl, p-chlorophenylacetyl, nicotinoyl or orotoyl; and X is hydroxyl, halo and especially chloro or $C_{1-5}$alkoxy.

The reaction may be carried out in an inert organic solvent such as toluene, xylene and especially benzene. The reaction is carried out at a temperature of from about 70° C to 140° C, preferably at the reflux temperature of the solvent. The time of reaction is not critical and the reaction is preferably carried out until it is essentially complete. The pressure is not critical and the reaction is generally carried out at atmospheric pressure in an open system. The ester may be recovered in the conventional manner such as by precipitation of the ester salt in a non-solvent for the product such as diethylether.

The formate ester may be prepared by reacting 2-(1-pyrrolidino)-ethanol with formic acid and gaseous hydrogen chloride at a temperature of from about −30° C to about 5° C until the reaction is essentially complete.

The monosuccinate ester may be prepared by reacting succinic anhydride with 2-(1-pyrrolidino)-ethanol in an inert solvent such as toluene, xylene and especially benzene at a temperature of from about 70° C to 140° C, preferably at the reflux temperature of the solvent until the reaction is essentially complete.

The effect of chick weight on feed consumption (in grams) per day and per kg of body weight for various aged broiler chicks is as follows:

| Age Weeks | Wt. (Avg) g | Feed Consumption Per Bird Per Day (Avg) g | Feed Consumption Per Kg Body Wt Per Day (Avg) g |
|---|---|---|---|
| 1 | 100 | 19.0 | 190 |
| 2 | 200 | 30.0 | 150 |
| 3 | 400 | 48.0 | 120 |
| 4 | 600 | 60.0 | 100 |
| 5 | 800 | 70.0 | 87 |
| 6 | 1050 | 88.0 | 84 |
| 7 | 1300 | 87.0 | 67 |
| 8 | 1450 | 95.0 | 65 |
| 9 | 1700 | 102.0 | 60 |
| 10 | 1950 | 111.0 | 57 |

The following examples are given to illustrate the invention and are not intended to limit it in any manner.

All parts are given in parts by weight unless otherwise expressed.

EXAMPLE 1

*E. acervulina* Assay

Three 11-day-old female White Leghorns, weighing between 75–90gm. each, were maintained on a vitamin-supplemented diet (Pennfield 180) containing the sample to be tested. One day later, each chicken was orally inoculated with $4 \times 10^5$ sporulated oocysts of *E. acervulina* and maintained on the same diet for five more days. Three parameters; relative weight gain, serum albumin levels, and internal duodenal lesion scores, were used to evaluate the extent of infection.

*E. tenella* Assay

By a similar experimental procedure, $10^5$ *E. tenella* sporulated oocysts were orally dosed to each chicken. Serum albumin levels were not measured. Instead, bloody droppings were scored as an indication of infection.

Following the above procedure, the following compounds were found to have a rating of "active" at the dose level shown:

| Compounds | Minimum effective concentration in % by weight | |
|---|---|---|
| | Et | Ea |
| 2-pyrrolidinoethanol | 0.1 | 0.2 |
| 2-piperidinoethanol | 0.2 | 0.2 |
| 2-pyrrolidinoethyl acetate . HCl | 0.05 | 0.2 |
| 2-pyrrolidinoethyl benzoate . HCl | 0.1 | 0.2 |
| 2-pyrrolidinoethyl nicotinate . HCl | 0.1 | 0.2 |
| 2-pyrrolidinoethyl orotate . HCl | 0.05 | 0.2 |
| 2-pyrrolidinoethyl p-chlorophenylacetate . HCl | 0.1 | 0.2 |
| 2-pyrrolidinoethyl 1-adamantylacetate . HCl | 0.05 | 0.2 |
| 2-pyrrolidinoethyl butyrate . HCl | 0.1 | 0.2 |
| 2-pyrrolidinoethyl formate . HCl | 0.1 | 0.2 |
| 2-pyrrolidinoethyl hexanoate . HCl | 0.05 | 0.2 |
| 2-pyrrolidinoethyl isobutanoate . HCl | 0.1 | 0.2 |
| 2-pyrrolidinoethyl p-nitrobenzoate . HCl | 0.05 | 0.2 |
| 2-pyrrolidinoethyl 1-adamantylcarboxylate . HCl | 0.05 | 0.2 |
| 2-pyrrolidinoethyl octanoate . HCl | 0.05 | 0.2 |
| 2-pyrrolidinoethyl diphenylacetate . HCl | 0.1 | 0.2 |
| 2-pyrrolidinoethyl monosuccinate | 0.05 | 0.2 |
| di-2-pyrrolidinoethyl adipate . 2HCl | 0.1 | 0.2 |

Et = *Eimeria tenella*
Ea = *Eimera acervulina*
* Composition of Basal Ration Analysis

| | |
|---|---|
| Crude Protein (minimum) | 21% |
| Crude Fat (minimum) | 5% |
| Crude Fiber (maximum) | 3% |

Ingredients

Corn gluten meal, $CaCO_3$, fish meal, dehulled soybean meal, ground corn, dicalcium phosphate, animal fat (preserved with butylated hydroxyanisole, anhydrous citric acid and propylene glycol), salt (NaCl), copper oxide, $FeSO_4$ calcium iodate, manganous oxide, ZnO, Vitamin A palmitate, D-activated animal sterols, α-tocopherol acetate (source of Vitamin E), Vitamin B-12, riboflavin, niacin, calcium pantothenate, choline chloride, menadione sodium bisulfite complex (source of Vitamin K), folic acid, ethoxyquin (a preservative), methionine hydroxy analogue calcium.

EXAMPLE 2

Coccidiostatic activity of 2-pyrrolidinoethanol, (PE) alone, and in combination with sulfaquinoxaline (SQ) was determined by the following method:

Groups of ten two-week-old chicks were fed a mash diet containing graded amounts of 2-pyrrolidinoethanol (PE), alone, and in combination with sulfaquinoxaline (SQ). The compound was uniformly dispersed in the basal ration (see Example 1, supra). After having been on this ration for 24 hours, each chick was inoculated with 50,000 sporulated oocysts of *Eimeria tenella*. Other groups of ten chicks were each fed a similar mash diet which contained no coccidiostat. These were also infected in the same manner after 24 hours and served as infected controls. As normal controls, two to four groups of ten chicks each were fed the mash feed of coccidiostat and were not infected with coccidiosis. These served as normal controls.

The diets were administered to the chicks for eight days following the date of infection. At the end of this time the infected birds were sacrified. The oocyst count was determined by a microscopic examination of the cecal homogenates.

The potentiating action of 2-pyrrolidinoethanol (PE) in coccidiosis control was experimentally demonstrated with sulfaquinoxaline (SQ).

The results employing the indicated amounts of coccidiostat compound, expressed as mean values, are set forth in the following table.

| Compound | Percent compound in feed | Percent weight gain | Percent survival | No. of Oocysts $\times 10^6$ in surviving birds |
|---|---|---|---|---|
| Infected Controls | — | 38 | 50 | 22.4 |
| Normal Controls | — | 113 | 100 | 0.0 |
| PE | 0.1 | 113 | 100 | 1.5 |
| PE | 0.05 | 102 | 80 | 5.5 |
| PE | 0.025 | 45 | 100 | 16.1 |
| SQ | 0.1 | 102 | 100 | 0.0 |
| SQ | 0.05 | 91 | 100 | 0.1 |
| SQ | 0.025 | 85 | 90 | 0.4 |
| PE/SQ | 0.05/0.025 | 127 | 100 | 0.0 |
| PE/sq | 0.05/0.0125 | 120 | 100 | 0.0 |
| PE/SQ | 0.025/0.05 | 122 | 100 | 0.0 |
| PE/SQ | 0.025/0.025 | 109 | 100 | 0.0 |
| PE/SQ | 0.025/0.0125 | 122 | 100 | 0.9 |
| PE/SQ | 0.0125/0.05 | 104 | 100 | 0.0 |
| PE/SQ | 0.0125/0.025 | 98 | 100 | 2.2 |
| PE/SQ | 0.0125/0.0125 | 106 | 100 | 6.9 |

EXAMPLE 3

Coccidiostatic activity of 2-pyrrolidinoethanol was determined using the test method of Example 2 for *Eimeria acervulina* with the following exceptions:

1. The test was terminated 6 days after infection.
2. Duodenal lesions rather than cecal lesions were scored.
3. Five birds were used instead of ten.
4. The inoculum size was 200,000 sporulated oocysts per bird instead of 50,000.
5. The oocyst count was determined by microscopic examination of fecal homogenate.

The potentiating action of 2-pyrrolidinoethanol (PE) in coccidiosis control was experimentally demonstrated with sulfaquinoxaline (SQ).

| Compound | Percent compound in feed | Percent weight gain | Percent survival | No. of Oocysts $\times 10^6$ in surviving birds |
|---|---|---|---|---|
| Infected Controls | — | 68 | 100 | 10.3 |
| Normal Controls | — | 137 | 100 | 0.0 |
| PE | 0.2 | 112 | 100 | 0.0 |
| PE | 0.1 | 143 | 100 | 0.7 |
| PE | 0.05 | 80 | 100 | 1.0 |
| SQ | 0.05 | 114 | 100 | 0.0 |
| SQ | 0.025 | 101 | 100 | 0.7 |
| SQ | 0.0125 | 102 | 100 | 2.7 |
| PE/SQ | 0.1/0.025 | 135 | 100 | 0.0 |
| PE/SQ | 0.05/0.025 | 118 | 100 | 0.0 |
| PE/SQ | 0.025/0.025 | 140 | 100 | 0.0 |
| PE/SQ | 0.0125/0.025 | 116 | 100 | 0.7 |
| PE/SQ | 0.1/0.0125 | 131 | 100 | 0.0 |
| PE/SQ | 0.05/0.0125 | 114 | 100 | 0.0 |
| PE/SQ | 0.025/0.0125 | 123 | 100 | 0.3 |
| PE/SQ | 0.0125/0.0125 | 58 | 100 | 4.3 |

EXAMPLE 4

Coccidiostatic activity of 2-pyrrolidinoethanol was determined using the test method of Example 2 for *Eimeria brunetti.*

The procedure was the same as that employed in the *Eimeria tenella* (see Example 2) assay with the following exceptions:

1. Mid- and lower-intestinal lesions were scored.
2. The inoculum size was 100,000 sporulated oocysts per bird.
3. The oocyst count was determined by microscopic examination of fecal homogenate.

The potentiating action of 2-pyrrolidinoethanol (PE) in coccidiosis control was experimentally demonstrated with sulfaquinoxaline (SQ).

| Compound | Percent compound in feed | Percent weight gain | Percent survival | No. of Oocysts $\times 10^6$ in surviving birds |
|---|---|---|---|---|
| Infected Controls | — | 52.1 | 100 | 7.8 |
| Normal Controls | — | 115.7 | 100 | 0.0 |
| PE | 0.2 | 88.5 | 100 | 0.1 |
| PE | 0.1 | 104.6 | 100 | 0.4 |
| PE | 0.05 | 86.2 | 100 | 1.1 |
| PE | 0.025 | 60.5 | 100 | 5.1 |
| SQ | 0.1 | 99.4 | 100 | 0.2 |
| SQ | 0.05 | 103.4 | 100 | 0.0 |
| SQ | 0.025 | 106.1 | 100 | 0.1 |
| SQ | 0.0125 | 77.0 | 100 | 5.9 |
| PE/SQ | 0.1/0.05 | 110.6 | 100 | 0.6 |
| PE/SQ | 0.05/0.05 | 116.2 | 100 | 0.1 |
| PE/SQ | 0.025/0.05 | 92.4 | 100 | 0.2 |
| PE/SQ | 0.0125/0.05 | 51.8 | 100 | 3.5 |
| PE/SQ | 0.1/0.025 | 111.2 | 100 | 0.0 |
| PE/SQ | 0.05/0.025 | 122.9 | 100 | 0.0 |
| PE/SQ | 0.025/0.025 | 94.5 | 100 | 0.0 |
| PE/SQ | 0.0125/0.025 | 52.4 | 100 | 3.2 |
| PE/SQ | 0.1/0.0125 | 100.6 | 100 | 0.2 |
| PE/SQ | 0.05/0.0125 | 112.0 | 100 | 0.1 |
| PE/SQ | 0.025/0.0125 | 84.8 | 100 | 1.4 |
| PE/SQ | 0.0125/0.0125 | 49.7 | 100 | 5.9 |
| PE/SQ | 0.1/0.006 | 108.3 | 100 | 0.0 |
| PE/SQ | 0.05/0.006 | 118.3 | 100 | 0.2 |
| PE/SQ | 0.025/0.006 | 84.9 | 100 | 1.8 |
| PE/SQ | 0.0125/0.006 | 55.0 | 100 | 3.6 |

EXAMPLE 5

Coccidiostatic activity of 2-pyrrolidinoethanol was determined using the test method of Example 2 for *Eimeria maxima* with the following exceptions:

1. Upper- and mid-intestinal lesions were scored.
2. The inoculum size was 100,000 sporulated oocysts per bird.

3. The oocyst count was determined by microscopic examination of fecal homogenate.

The potentiating action of 2-pyrrolidinoethanol (PAE) in coccidiosis control was experimentally demonstrated with sulfaquinoxaline

| Compound | Percent compound in feed | Percent weight gain | Percent survival | No. of Oocysts × $10^6$ in surviving birds |
|---|---|---|---|---|
| Infected Controls | — | 71.6 | 100 | 6.5 |
| Normal Controls | — | 125.8 | 100 | 0.0 |
| PE | 0.2 | 71.5 | 100 | 0.1 |
| PE | 0.1 | 54.2 | 100 | 1.3 |
| PE | 0.05 | 47.9 | 100 | 9.7 |
| SQ | 0.1 | 94.5 | 100 | 0.0 |
| SQ | 0.05 | 100.3 | 100 | 0.5 |
| SQ | 0.025 | 86.2 | 100 | 0.2 |
| SQ | 0.0125 | 89.2 | 100 | 4.7 |
| SQ | 0.006 | 73.8 | 100 | 10.2 |
| PE/SQ | 0.1/0.05 | 100.9 | 100 | 0.0 |
| PE/SQ | 0.05/0.05 | 111.7 | 100 | 0.0 |
| PE/SQ | 0.025/0.05 | 104.6 | 100 | 0.1 |
| PE/SQ | 0.0125/0.05 | 99.3 | 100 | 0.0 |
| PE/SQ | 0.1/0.025 | 98.2 | 100 | 3.0 |
| PE/SQ | 0.05/0.025 | 119.2 | 100 | 0.1 |
| PE/SQ | 0.025/0.025 | 97.9 | 100 | 2.5 |
| PE/SQ | 0.0125/0.025 | 90.8 | 100 | 4.3 |
| PE/SQ | 0.1/0.0125 | 77.2 | 100 | 2.1 |
| PE/SQ | 0.05/0.0125 | 88.5 | 100 | 0.0 |
| PE/SQ | 0.025/0.0125 | 80.2 | 100 | 5.0 |
| PE/SQ | 0.0125/0.0125 | 64.5 | 100 | 3.4 |
| PE/SQ | 0.1/0.006 | 40.8 | 100 | 1.7 |
| PE/SQ | 0.05/0.006 | 69.7 | 100 | 5.9 |
| PE/SQ | 0.025/0.006 | 66.2 | 100 | 10.1 |
| PE/SQ | 0.0125/0.006 | 65.1 | 100 | 4.0 |

EXAMPLE 6

Coccidiostatic activity of 2-pyrrolidinoethanol was determined using the test method of Example 2 for *Eimeria necatrix*.

The procedure was the same as that employed in the *Eimeria tenella* (see Example 2) assay with the following exceptions:

1. Mid- and Lower-intestinal lesions were scored.
2. The inoculum size was 100,000 sporulated oocysts per bird.
3. The oocyst count was determined by microscopic examination of fecal homogenate.

| Compound | Percent compound in feed | Percent weight gain | Percent survival | No. of Oocysts × $10^6$ in surviving birds |
|---|---|---|---|---|
| Infected Control | — | 77.7 | 100 | 8.7 |
| Normal Control | — | 127.0 | 100 | 0.0 |
| PE | 0.1 | 113.9 | 100 | 0.0 |
| PE | 0.05 | 93.4 | 100 | 2.9 |

EXAMPLE 7

Coccidiostatic activity of 2-pyrrolidin ethanol was determined alone, and in combination with sulfaquinoxaline (SQ) and pyrimethamine (PYR).

The potentiating action of 2-pyrrolidinoethanol (PE) in coccidiosis control was experimentally demonstrated with sulfaquinoxalines (SQ) and pyrimethamine (PYR).

Two-week-old sex-and weight- balanced white cross chicks in groups of 10 were placed in pens and fed a standard commercial ration to which drugs were added just prior to use. The uninfected and infected control birds were fed the basal ration. Pen locations of all groups were randomized. On the second day of the test the chicks except for uninfected conrols were inoculated orally with the following numbers of sporulated oocysts: *Eimeria tenella*, 50,000; *E. necatrix*, 50,000; *E. maxima*, 100,000; *E. brunetti*, 100,000; *E. acervulina*, 200,000.

Several criteria were employed for evaluation of anticoccidial efficacy. These included observations and records on mortality rate, growth, severity of pathological lesions, and number of oocysts produced. coccidial lesions were scored according to the following system: 0=normal, 1=detectable, 2=moderate, 3=marked, 4=maximal. To obtain estimates of oocyst production, the feces were homogenized in a blender. Appropriate aliquots were diluted, placed in a hemocytometer and counted.

| Compound | Percent compound in feed (by weight) | Percent weight gain | Percent survival |
|---|---|---|---|
| Infected Control | — | 25 | 8 |
| Normal Control | — | 127 | 100 |
| PE | 0.2 | 36 | 100 |
| PE | 0.1 | 46 | 100 |
| PE | 0.05 | 64 | 100 |
| SQ/PYR | 0.006/.0005 | 45 | 60 |
| PE/SQ/PYR | 0.1/0.006/0.0005 | 136 | 100 |
| PE/SQ/PYR | 0.05/0.006/0.0005 | 139 | 100 |
| PE/SQ/PYR | 0.025/0.006/0.0005 | 111 | 100 |
| PE/SQ/PYR | 0.0125/0.006/0.0005 | 88 | 100 |

| Compound | Percent compound in feed (by weight) | Lesion score Cecum | Lesion score Intest. | Lesion score Duod |
|---|---|---|---|---|
| Infected Control | — | 3.9 | 2.3 | 3.3 |
| Normal Control | — | 0.0 | 0.0 | 0.0 |
| PE | 0.2 | 0.5 | 1.2 | 3.2 |
| PE | 0.1 | 0.3 | 0.3 | 3.2 |
| PE | 0.05 | 1.6 | 0.6 | 0.8 |
| SQ/PYR | 0.006/0.0005 | 4.0 | 2.1 | 1.6 |
| PE/SQ/PYR | 0.1/0.006/0.0005 | 0.0 | 0.1 | 0.0 |
| PE/SQ/PYR | 0.05/0.006/0.00 | 0.0 | 0.0 | 0.2 |
| PE/SQ/PYR | 0.025/0.006/0.0005 | 1.3 | 1.6 | 1.3 |
| PE/SQ/PYR | 0.0125/0.006/0.0005 | 3.4 | 0.8 | 0.4 |

| Compound | Percent compound in feed (by weight) | No. of Oocysts × $10^6$ in surviving birds Small | Medium | Large |
|---|---|---|---|---|
| Infected Control | — | 16.0 | 36.5 | 11.0 |
| Normal Control | — | 0.1 | 0.2 | 0.3 |
| PE | 0.2 | 0.9 | 0.6 | 0.3 |
| PE | 0.1 | 0.3 | 0.1 | 0.4 |
| PE | 0.05 | 0.7 | 0.8 | 1.1 |
| SQ/PYR | 0.006/0.0005 | 7.0 | 6.8 | 0.1 |
| PE/SQ/PYR | 0.1/0.006/0.0005 | 0.1 | 0.1 | 0.1 |
| PE/SQ/PYR | 0.05/0.006/0.0005 | 0.6 | 0.3 | 0.1 |
| PE/SQ/PYR | 0.025/0.006/0.0005 | 1.6 | 1.6 | 0.1 |
| PE/SQ/PYR | 0.0125/0.006/0.0005 | 5.1 | 10.0 | 0.1 |

EXAMPLE 8

2-(1-Azetidino)-ethanol

A mixture of 5.7 g of azetidine and 12.9 g of diisopropylethylamine is heated to 70° C in a nitrogen atmosphere and 12.5 g of 2-bromoethanol is added dropwise with stirring. After one hour at 70° C, the reaction mixture is cooled to room temperature and extracted with ether. The ether extracts are filtered and evaporated to give 2-(1-azetidino)-ethanol.

EXAMPLE 9 2-(1-Pyrrolidino)-ethyl butyrate.HCl

To a solution of 11.5 g of 2-(1-pyrrolidino) ethanol (0.10 moles) in 50 ml of benzene is added all at once a solution of 10.7g(0.10 moles) of butyryl chloride in 50 ml of benzene. The mixture is heated under reflux for two hours, cooled and poured into 500 ml of diethylether to precipitate the product, m.p. 108°-110° C.

Following the procedure above, when an equivalent amount of the following carboxylic acid chlorides are substituted for the butyryl chloride in the above example, the following products are obtained.

| Carboxylic acid chloride | Product | M.P. |
|---|---|---|
| isobutyryl chloride | 2-(1-pyrrolidino)-ethyl isobutyrate . HCl | 98–100° C |
| hexanoyl chloride | 2-(1-pyrrolidino)-ethyl hexanoate . HCl | 105–106° C |
| octanoyl chloride | 2-(1-pyrrolidino)-ethyl octanoate . HCl | 118–119° C |
| 1-adamantylacetyl chloride | 2-(1-pyrrolidino)-ethyl 1-adamantylacetate . HCl | 207–208° C |
| 1-adamantylcarbonyl chloride | 2-(1-pyrrolidino)-ethyl 1-adamantylcarboxylate . HCl | 170–173° C |
| p-chlorophenylacetyl chloride | 2-(1-pyrrolidino)-ethyl p-chlorophenylacetate . HCl | 114° C |
| nicotinoyl chloride | 2-(1-pyrrolidino)-ethyl nicotinate . 2HCl | 159–161° C |
| orotoyl chloride | 2-(1-pyrrolidino)-ethyl orotate . HCl | dec. 247–250° C |

EXAMPLE 10

2-(1-pyrrolidino)ethyl formate.hydrogen chloride

A solution of 11.5 g of 2-(1-pyrrolidino)ethanol in 25 ml of formic acid (97-100%) is cooled to −5° C. Hydrogen chloride gas is bubbled into the solution for 2 hours while maintaining the temperature at 0° C. After standing at room temperature for two days the mixture is evaporated to dryness under reduced pressure. The residue is dissolved in chloroform and poured into diethylether. The gummy precipitate is recrystallized from a 50/50 mixture of isopropanol and diethylether to give the product m.p. 58° C.

EXAMPLE 11

2-(1-pyrrolidino)ethyl monosuccinate

A mixture of 11.5 g of 2-(1-pyrrolidino)-ethanol, 10 g of succinic anhydride and 120 ml of benzene is heated under reflux for 1 ½ hours. The mixture is cooled and evaporated under reduced pressure. The residue is dissolved in chloroform, filtered and concentrated to dryness under reduced pressure. The residue is recrystallized from ethyl acetate to give the product m.p. 80°–82° C.

Any departure from the above description which conforms to the present invention is intended to be included within the scope of the claims.

What is claimed is:

1. An anticoccidial composition comprising an anticoccidially effective amount of a cyclicamino ethanol compound of the formula:

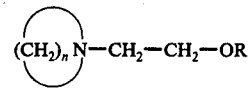

wherein R is hydrogen or an acyl radical derived from a non-toxic carboxylic acid selected from the group consisting of $C_{1-10}$ alkanoyl; substituted $C_{1-5}$ alkanoyl wherein the substituent is halophenyl and diphenyl; carbocyclic alkanoyl containing up to 5 carbon atoms; benxoyl; nitrobenzoyl; nicotinyl, orotoyl; and $C_{1-10}$ alkane dicarbonyl; wherein n is 3, 4 or 5 or a non-toxic acid addition salt thereof, in a chicken feed.

2. The anticoccidial composition of claim 1 wherein n is 4 and R is hydrogen, $C_{1-10}$ alkanoyl, substituted $C_{1-5}$ alkanoyl wherein the substituent is halophenyl or diphenyl; carbocyclic alkanoyl containing up to 5 carbon atoms, benzoyl, nitrobenzoyl, nicotinyl, orotoyl; or $C_{1-10}$ alkane dicarbonyl.

3. The anticoccidial composition of claim 2 wherein R is hydrogen, acetyl, benzoyl, nicotinyl, orotoyl, p-chlorophenylacetyl, butyryl, formyl, hexanoyl, isobutyroyl, p-nitrobenzoyl, octanoyl, diphenylacetyl, adipoyl or monosuccinyl.

4. The anticoccidial composition of claim 3 wherein R is hydrogen, acetyl, hexanoyl, octanoyl, p-nitrobenzoyl, orotoyl, adipyl or monosuccinyl.

5. The anticoccidial composition of claim 1 wherein 2-pyrrolidinoethanol is used.

6. The anticoccidial composition of claim 1 wherein an anticoccidially effective amount of sulfa drug is present as an additional ingredient.

7. The anticoccidial composition of claim 6 wherein the sulfa drug is sulfabenz, sulfachloropyrazine, sulfachloropyridazine, sulfadiazine, sulfadimethoxine, sulfaguanidine, sulfamerazine, sulfamethazine, sulfanitran, sulfaquinoxaline or a compound of the formula:

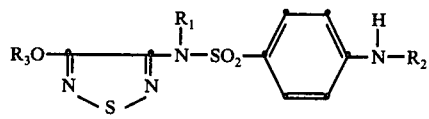

wherein $R_3$ is $C_{2-5}$alkenyl selected from the group consisting of allyl, methallyl and crotyl; $C_{2-5}$alkynyl, selected from the group consisting of 2-butynyl, 3-butynyl and 2-propynyl; $C_{2-5}$alkyl selected from the group consisting of ethyl, n-propyl, isopropyl and butyl; $R_1$ is hydrogen, an alkali metal; and $R_2$ is hydrogen; acyl, selected from the group consisting of benzoyl and $C_{1-5}$alkanoyl, wherein $C_{1-5}$ alkanoyl is selected from the group consisting of acetyl, propionyl and butyryl.

8. The anticoccidial composition of claim 7 wherein sulfaquinoxaline is used.

9. The anticoccidial composition of claim 6 wherein an anticoccidially effective amount of 2,4-diamino-5-phenyl-6-$C_{1-5}$alkyl pyrimidine; 2,4-diamino-5- benzyl-6-$C_{1-5}$alkyl pyrimidine; 2,4-diamino-5-phenyl pyrimidine; or 2,4-diamino-5-benzyl pyrimidine is present as an additional ingredient.

10. The anticoccidial composition of claim 9 wherein said active anticoccidial ingredient is a mixture of about 0.0125 to 0.2% (by weight of feed) of a cyclicaminoethanol or an ester thereof, 0.005 to 0.1% of a sulfa drug and 0.0001 to 0.0001% of 2,4-diamino-5-phenyl-6-$C_{1-5}$ alkyl pyrimidine; 2,4-diamino-5-benzyl-6-$C_{1-5}$alkyl pyrimidine; 2,4-diamino-5-phenyl pyrimidine or 2,4-diamino-5-benzyl pyrimidine.

11. The anticoccidial composition of claim 1 in a formulation premix of from about 5% to 40% by weight.

12. The anticoccidial composition of claim 6 in a formulation premix of from about 5% to 40% by weight.

13. The anticoccidial composition of claim 9 in a formulation premix of from about 5% to 40% by weight.

14. The anticoccidial composition of claim 1 wherein said active anticoccidial ingredient is present to the extent of about 0.2 to about 0.025% by weight of poultry feed.

15. An anticoccidial composition comprising an anticoccidially effective amount of a cyclicamino ethanol compound of the formula:

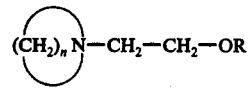

wherein
  $n$ is 3, 4 or 5 and R is 1-adamantylacetyl or 1-adamantylcarbonyl in a poultry feed.